US010485495B2

(12) United States Patent
Congy et al.

(10) Patent No.: US 10,485,495 B2
(45) Date of Patent: Nov. 26, 2019

(54) HAND POSITIONER FOR CEPHALOMETRIC EXTRA ORAL DENTAL IMAGING DEVICES

(71) Applicant: TROPHY, Croissy Beaubourg (FR)

(72) Inventors: Philippe Congy, Croissy Beaubourg (FR); Olivier Martino, Croissy Beaubourg (FR)

(73) Assignee: TROPHY, Croissy Beaubourg (FR)

( * ) Notice: Subject to any disclaimer, the term of this patent is extended or adjusted under 35 U.S.C. 154(b) by 317 days.

(21) Appl. No.: 15/524,767

(22) PCT Filed: Jan. 14, 2015

(86) PCT No.: PCT/IB2015/000339
§ 371 (c)(1),
(2) Date: May 5, 2017

(87) PCT Pub. No.: WO2016/087911
PCT Pub. Date: Jun. 9, 2016

(65) Prior Publication Data
US 2017/0325760 A1 Nov. 16, 2017

Related U.S. Application Data

(60) Provisional application No. 62/087,374, filed on Dec. 4, 2014.

(51) Int. Cl.
*A61B 6/14* (2006.01)
*A61B 6/04* (2006.01)
*A61B 6/00* (2006.01)

(52) U.S. Cl.
CPC ............. *A61B 6/0421* (2013.01); *A61B 6/14* (2013.01); *A61B 6/505* (2013.01)

(58) Field of Classification Search
CPC .......... A61B 6/0421; A61B 6/14; A61B 6/505
(Continued)

(56) References Cited

U.S. PATENT DOCUMENTS

| 5,511,106 A | 4/1996 | Doebert et al. |
| 2009/0196395 A1* | 8/2009 | Gregorio .................. A61B 6/14 |
| | | 378/38 |

(Continued)

FOREIGN PATENT DOCUMENTS

| EP | 2 609 860 A1 | 7/2013 |
| EP | 3 226 771 A1 | 10/2017 |

(Continued)

OTHER PUBLICATIONS

International Search Report, International application No. PCT/US2015/000339, dated Jul. 29, 2015, 2 pages.

(Continued)

*Primary Examiner* — Courtney D Thomas (57) ABSTRACT

A hand positioner device for an extra-oral imaging system can be coupled to the cephalometric mount between the collimator and the cephalometric sensor. The hand positioner device is attached and detached from the cephalometric mount without using tools. In one embodiment, a hand positioner device for an extra-oral imaging system can have an adjustable level of attachment. In one embodiment, a hand positioner device for an extra-oral imaging system can be repeatedly mounted in a plane parallel to an imaging plane of the cephalometric sensor.

15 Claims, 8 Drawing Sheets

(58) Field of Classification Search
USPC .................................................. 378/38–40
See application file for complete search history.

(56) References Cited

U.S. PATENT DOCUMENTS

2011/0142197 A1 6/2011 Walker et al.
2012/0148031 A1 6/2012 Eaves

FOREIGN PATENT DOCUMENTS

| JP | 2011-019688 A | 2/2011 |
| JP | 2017-529710 A | 12/2017 |
| KR | 10-2017-0089873 A | 8/2017 |
| WO | 03/049615 A1 | 6/2003 |
| WO | 2013/110611 A1 | 8/2013 |
| WO | 2016/087911 A1 | 6/2016 |

OTHER PUBLICATIONS

Notification of Reasons for Refusal received for Japanese Patent Application Serial No. 2017-529710 dated Aug. 28, 2018, 3 pages.
International Preliminary Report on Patentability received for International Patent Application Serial No. PCT/IB2015/000339 dated Jun. 15, 2017, 7 pages.
Communication under Rule 71(3) EPC for European Patent Application Serial No. 15715402.2 dated Jul. 12, 2018, 64 pages.

* cited by examiner

HAND POSITIONER FOR CEPHALOMETRIC EXTRA ORAL DENTAL IMAGING DEVICES

CROSS REFERENCE TO RELATED APPLICATIONS

This application claims the benefit of and is a U.S. National Phase filing of PCT Application PCT/IB15/00339 filed Jan. 14, 2015, entitled "HAND POSITIONER FOR CEPHALOMETRIC EXTRA ORAL DENTAL IMAGING DEVICES", in the name of Congy et al., which claims the benefit of U.S. Provisional application U.S. Ser. No. 62/087,374, provisionally filed on Dec. 4, 2014 entitled "HAND POSITIONER FOR CEPHALOMETRIC EXTRA ORAL DENTAL IMAGING DEVICES", in the names of Congy et al., all of which are incorporated herein by reference in their entirety.

FIELD OF THE INVENTION

The invention relates generally to the field of dental x-ray imaging, and more particularly, to imaging in a cephalometric x-ray mode for dental applications. Further, the invention relates to a combined cephalometric, panoramic and computed tomography dental imaging apparatus and/or methods.

BACKGROUND

In the dental imaging field, a cephalometric imaging device includes an x-ray source that emits a conical or pyramidal shaped x-ray beam towards a cephalometric imaging sensor mounted at the end of a long arm. A patient's positioning unit to position the patient's head is located between the x-ray source and the cephalometric sensor at the vicinity of the cephalometric sensor. Then, the x-ray beam originating from the remote x-ray source radiates the patient's skull before impinging the cephalometric sensor. The digitalization of the signal and the treatment of the data lead to the reconstruction of a projection image of the skull or at least a part of the skull of the patient.

In a general dental cephalometric imaging device, a distance between the x-ray source and the cephalometric sensor is large, typically 1.7 m. As the patient's positioning unit is located at the vicinity of the cephalometric sensor and away from the x-ray source, the magnitude ratio of the image size to the patient's skull size is close to 1 for any part of the skull.

The cephalometric sensor can have the shape of a thin vertical rectangle with a large (e.g., typically 30) height-to-width ratio. A collimator having the same shape as the cephalometric sensor is used to collimate the x-ray beam originating from the remote x-ray source. This collimator is positioned in front of the patient's positioning unit and in coincidence with the cephalometric sensor so that the x-ray beam is shaped before radiating the patient. The cephalometric imaging process includes accumulating frames of data from the cephalometric sensor while the cephalometric sensor is translated from one side of the skull to the other side (e.g., horizontally, vertically) with a combined and coordinated movement of the collimator. The frames of data are then merged and treated to reconstruct a projection image of the whole skull. In the cephalometric or skull imaging technique, the patient can be positioned facing the x-ray beam or in a profile position.

There is still a need for improved cephalometric functionality for dental imaging apparatus and/or methods.

SUMMARY

An aspect of this application is to advance the art of medical digital radiography, particularly for dental applications.

Another aspect of this application is to address, in whole or in part, at least the foregoing and other deficiencies in the related art.

It is another aspect of this application to provide, in whole or in part, at least the advantages described herein.

An advantage offered by apparatus and/or method embodiments of the application relates to improved imaging of teeth, jaw and head features or surfaces at a lower cost over conventional imaging methods.

An advantage offered by apparatus and/or method embodiments of the application relates to providing a hand positioning functionality for a dental cephalometric imaging apparatus.

An advantage offered by apparatus and/or method embodiments of the application relates to providing hand positioning functionality that can be installed without tools for a dental cephalometric imaging appartus.

An advantage offered by apparatus and/or method embodiments of the application relates to providing hand positioning device and/or methods that provide concurrent and/or detectable information when a hand positioner is installed and/or removed for subsequent imaging operations.

An advantage offered by apparatus and/or method embodiments of the application relates to providing a hand positioner for a dental cephalometric imaging apparatus that includes correct alignment upon installation.

According to one aspect of the disclosure, there is provided INDEPENDENT APPARATUS CLAIM in paragraph form.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

DESCRIPTION OF EXEMPLARY EMBODIMENTS

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

In the dental treatment field and especially in the orthodontics field, the dentist may need to know the age and/or the progress of the bone growth of a young patient before determining any orthodontics treatment. Actually, an orthodontics treatment should neither be started to soon nor too late in view of the anatomical development of the young patient. An x-ray imaging of the carpus, which is a cluster of bones located between the hand and the forearm, provides the practitioner with precise information about age and bone growth of the young patient.

In practice, an x-ray image of the whole patient's hand is carried out to obtain the information of the carpus. As the hand has more or less the same size as the head, the hand x-ray imaging can be carried out using a cephalometric x-ray imaging device. According to the prior art, a plate transparent to x-rays and having a size slightly bigger than the size of a hand is hung vertically parallel to and in front of the x-ray sensor. The patient then presses his hand against the plate, and in so doing, properly positions the hand before the cephalometric x-ray scanning.

Further according to the prior art, a cephalometric imaging device can include a base that can be vertically adjustable and that supports a cephalometric module. The cephalometric module includes a mount provided with housings and rails to hang and/or slide the various elements necessary for the cephalometric imaging process, namely a collimator to shape the x-ray beam, a patient's head positioning unit, a hand plate/positioner for carpus imaging, and an x-ray sensor to collect the x-ray beam after the x-ray beam has radiated either the head or the hand of the patient. However, disadvantages of the prior art cephalometric imaging device remain. One disadvantage is that the patient's head positioning unit can not be positioned (e.g., rotated) properly when the patient's hand plate/positioner is installed to the cephalometric mount and in place. As a consequence, the prior art hand's positioner/plate must be removed after it is used. Moreover, though the hand's plate/positioner is transparent to x-rays, the prior art hand plate/positioner would nevertheless at least slightly pollute a skull image if the x-ray beam had to pass through the hand's plate/positioner remaining in place before impinging the cephalometric sensor.

Another disadvantage presented by the hand's positioners according to the prior art is that the hand's positioners are difficult to remove from and to install onto the cephalometric mount. Another disadvantage presented by the hand's positioners according to the prior art is that there is no indication whether or not the hand's positioners are properly mounted onto or engaged in the cephalometric mounts.

There is still a need for a cephalometric imaging system with a cephalometric mount and a hand positioner including easy installation onto the cephalometric mount and/or the capability to provide the information that the hand positioner is actually and properly installed onto in the cephalometric mount.

Figure 1:
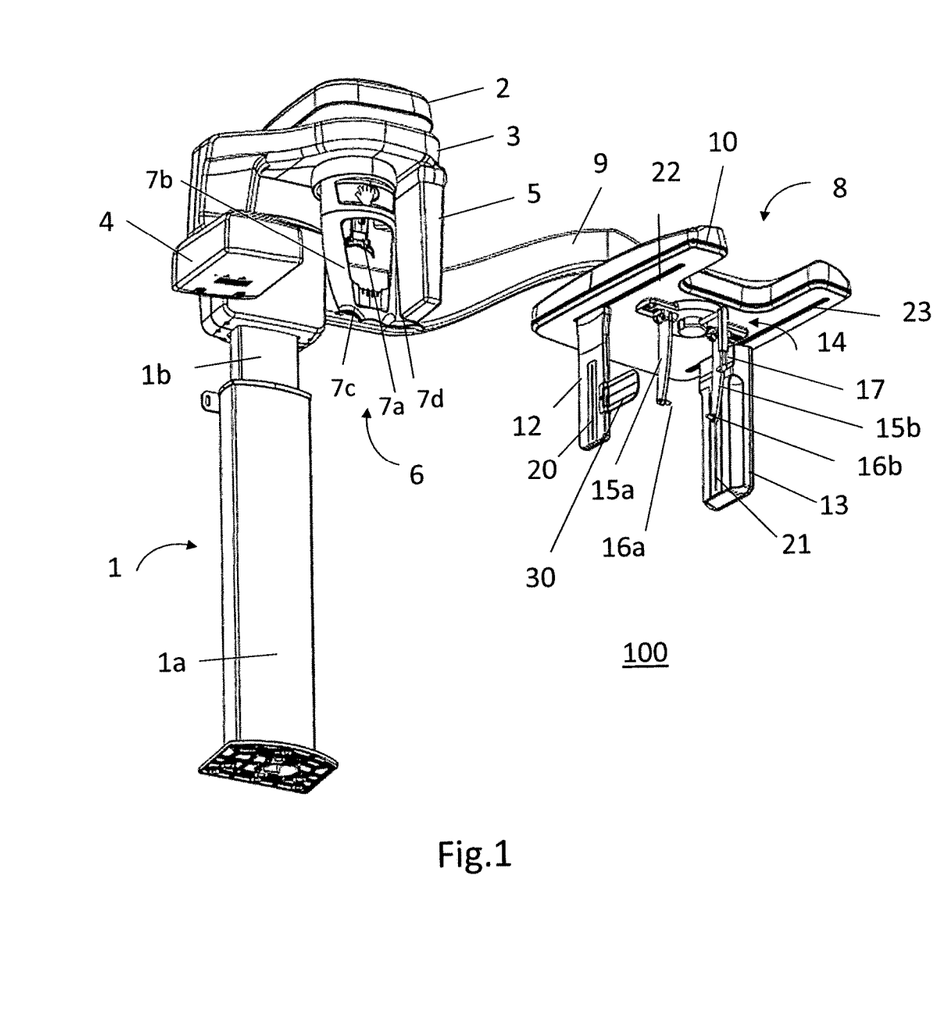
FIG. 1 is a diagram that shows a perspective view of a related art extra-oral dental imaging system including a cephalometric imaging unit.

FIG. 1 is a diagram that shows a perspective view of a related art extra-oral dental imaging system including a cephalometric imaging unit. As shown in FIG. 1, an exemplary extra-oral dental imaging system 100 includes a support structure that can include a support column 1. The column 1 may be adjustable in two-dimensions or three-dimensions. For example, the column 1 can be telescopic and may include an upper part 1*b* sliding inside a lower part 1*a*. A horizontal mount 2 may be supported or held by the vertical column 1 and can support a rotatable gantry 3. An x-ray source 4 and a first x-ray imaging sensor 5 can be attached or coupled to the gantry 3 in correspondence (e.g., opposite, aligned) to each other. The first x-ray sensor 5 may be a panoramic (e.g., slit-shaped) sensor or a Computerized Tomography (e.g., rectangular, square-shaped) sensor. Preferably, the x-ray beam originating from the x-ray source 4 impinges the sensor 5 after radiating a first imaging area, a subject or the patient. A first patient positioning and holding system 6 can be operatively positioned near or in the first imaging area. For example, the first patient positioning and holding system 6 may be between the x-ray source 4 and the first x-ray imaging sensor 5. The first patient positioning and holding system 6 can include a forehead support 7*a* and a shield 7*b* including two handles 7*c* and 7*d*. The patient can then grasp the handles 7*c* and 7*d* and remain motionless during the CT scan or panoramic scan.

More remote from the x-ray source 4, a cephalometric imaging unit 8 may be held in correspondence to the x-ray source 4. For example, as shown in FIG. 1, the cephalometric imaging unit 8 can be attached or coupled to the upper part 1*b* of the vertical column via an extended (e.g., horizontal) cephalometric arm 9. The cephalometric imaging unit 8 can include a mount 10 supporting a collimator 12, a second or cephalometric sensor 13 and a second patient positioning and holding system 14. As can also be seen in FIG. 2, the second patient positioning and holding system 14 can include a forehead support 17 and two temporal holding members 15*a* and 15*b*, each supporting an ear rod 16*a* and 16*b*. Preferably, the x-ray beam originating from the x-ray source 4 impinges the sensor 13 after radiating a second or cephalometric imaging area or the patient. The second patient positioning and holding system 14 can be operatively positioned near or in the second imaging area. For example, thanks to the second patient positioning and holding system 14, the patient is precisely and repeatedly positioned between the collimator 12 and the sensor 13, preferably in the second imaging area. One or more of the holding members 15a and 15b can respectively slide along rails 15ar and 15br so that the distance between the two ear rods 16a and 16b can be changed to fit the patient's head. The forehead support 17 can also be adjustable. For example, the forehead support 17 can be adjustable at least in two orthogonal dimensions by sliding along the horizontal and vertical directions. Alternatively, the forehead support 17 can be adjustable in three-dimensions or around three or more orthogonal axis.

Figure 2:
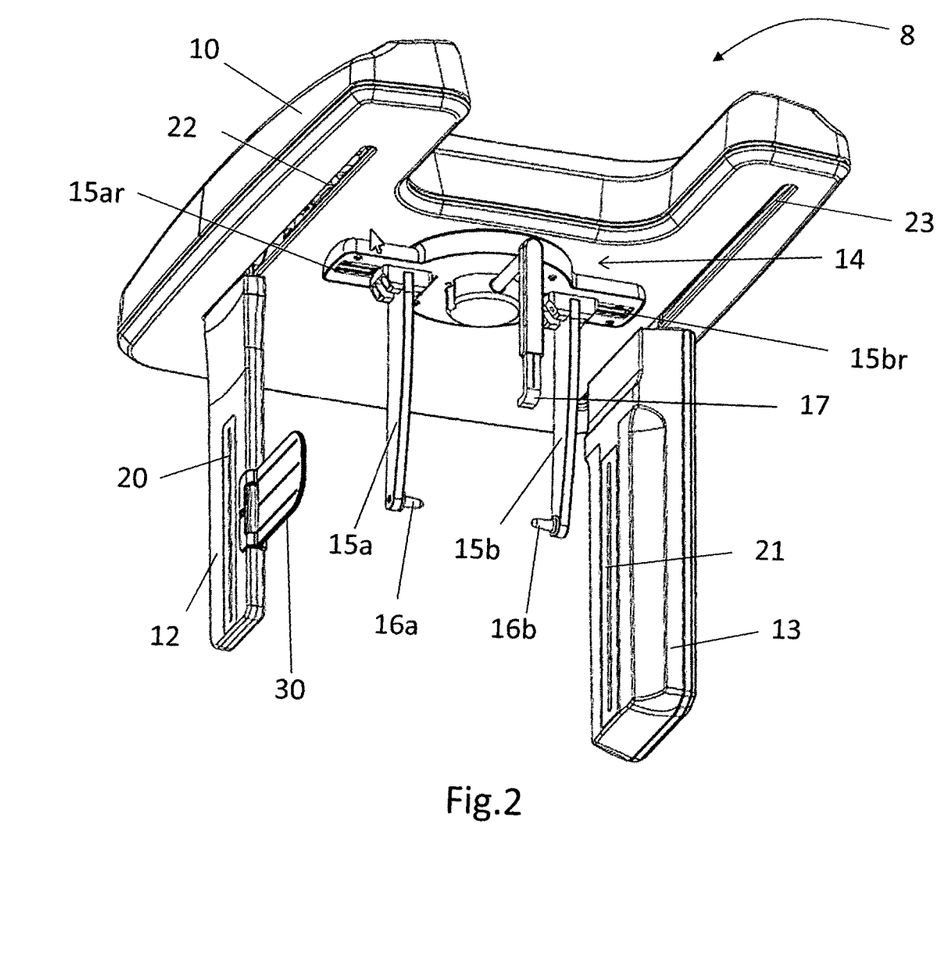
FIG. 2 is a diagram that shows a perspective view of a cephalometric imaging unit of FIG. 1.

As shown in FIG. 2, the collimator 12 can include an elongated opening or slit 20 to shape an x-ray beam. The x-ray sensor 13 can include an active area 21 having an elongated shape (e.g., a vertical slit) facing the vertical slit 20 of the collimator 12 (e.g., across the second imaging area). The sensor 13 and the collimator 12 face each other so that the sensor 13 can receive the x-rays originating from the x-ray source 4 after the x-ray beam was shaped by the collimator 12 and after the x-ray beam radiated the patient positioned and held on the second patient's positioning and holding system 14. For the scanning of the complete skull of the patient, the collimator 12 can move or slide during the x-ray scan along a rail 22 and the sensor 13 can move or slide along the rail 23, both rails being coupled to the mount 10. For example, the rails 22, 23 can be embodied on a lower face of the mount 10 of the cephalometric imaging unit 8. At any time during the cephalometric x-ray scan, an alignment may exist between a primary collimator in front of the source (not shown), the slit 20 of the collimator 12 and the active area of the sensor 13. Such x-ray alignment is disclosed, for example, in U.S. Pat. No. 5,511,106. At selected positions of the ensemble during the cephalometric scan, an x-ray digital image is obtained by the sensor 13. At the end of the cephalometric scan, an image reconstructing device (e.g., hardware, software and/or image processing) reconstructs the whole skull image on the basis of the plurality of images obtained during the cephalometric scan, for example using algorithms known to the person skilled in the art.

For a correct patient's positioning allowing a good image quality in the exemplary extra-oral dental imaging system 100, the Frankfort plane containing a straight line passing though the bottom of the eye socket and the ear canal must be horizontal. For the purpose of controlling or verifying that the Frankfort plane is horizontal, an at least partially transparent visual indicator 30 can be used.

Figure 3A:
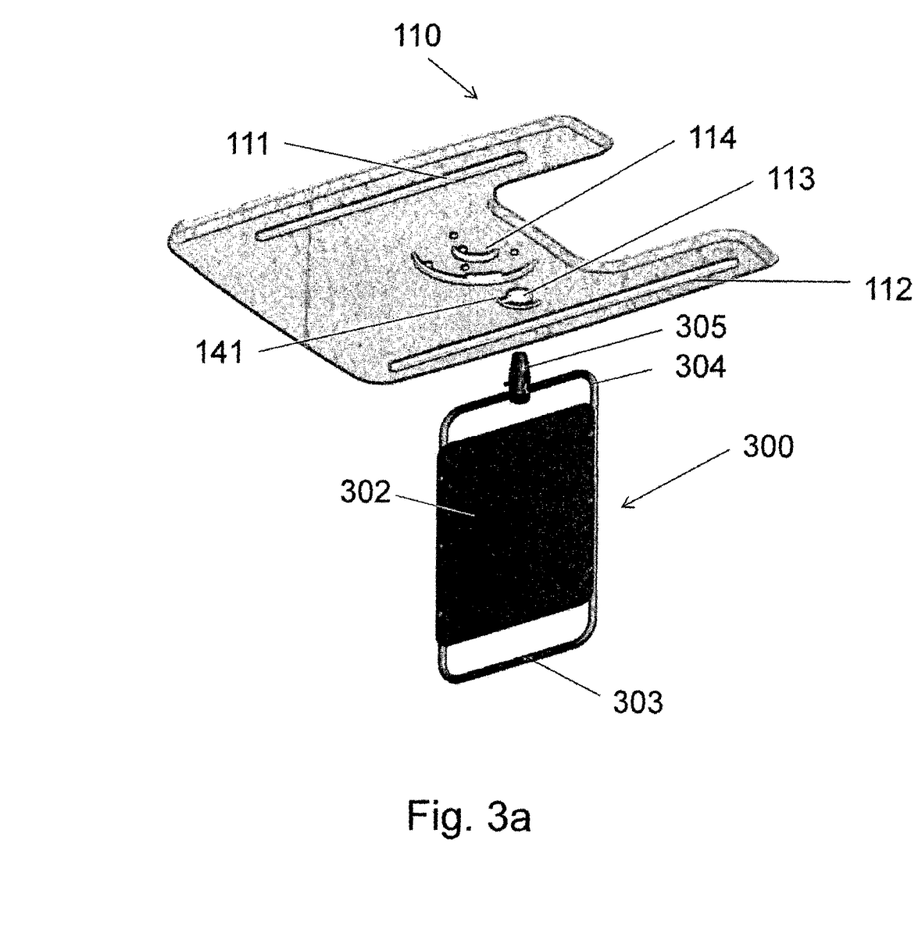
FIG. 3a is a diagram that shows a ensemble cephalometric mount and an exemplary hand positioner embodiment in a disengaged state.
Figure 3B:
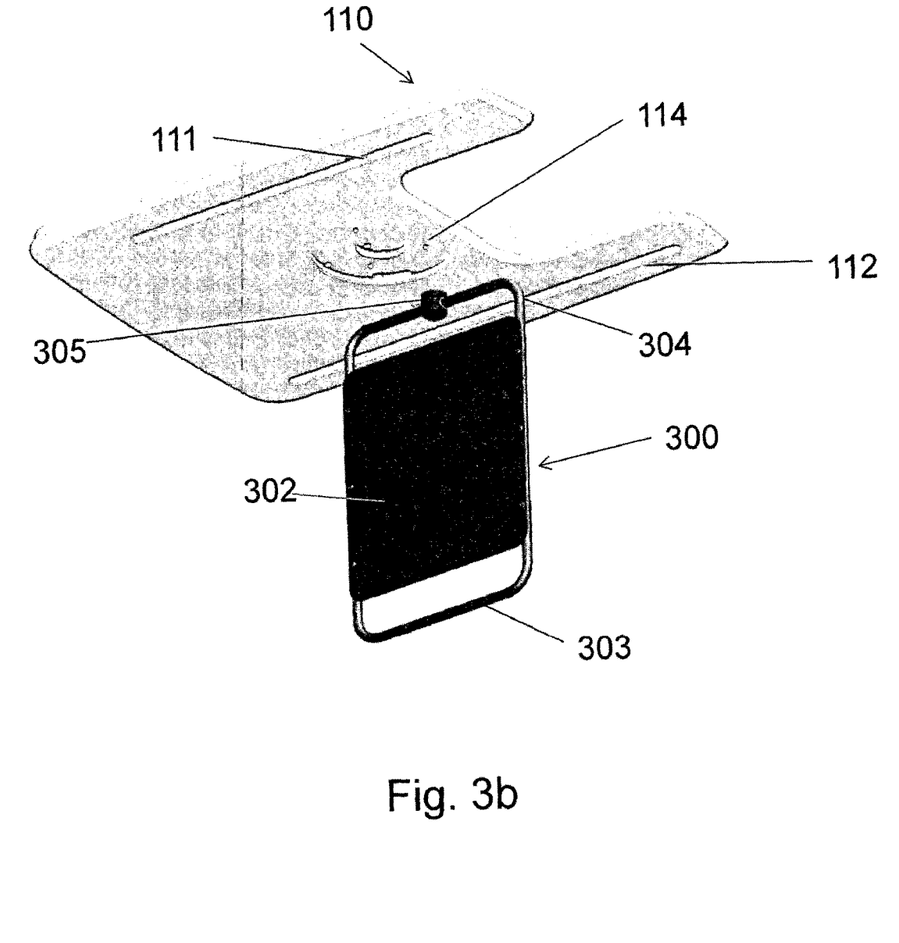
FIG. 3*b* is a diagram that shows a ensemble cephalometric mount and an exemplary hand positioner embodiment in an engaged state.

FIG. 3a is a diagram that shows an ensemble cephalometric mount and an exemplary hand positioner embodiment in a disengaged state. FIG. 3b is a diagram that shows an ensemble cephalometric mount and an exemplary hand positioner embodiment in an engaged state. As shown in FIGS. 3a-3b, an exemplary hand positioner embodiment can be applied to the related art extra-oral dental imaging system shown in FIG. 1.

As shown in FIG. 3a, a hand's positioner 300 can include a plate 302 that is transparent to x-rays incorporated into a frame (e.g., made of aluminum, metal, rigid materials, plastic, etc) including two handles 303 and 304 so that the positioner 300 can be grasped or easily manipulated by the practitioner. Other known versions of an area or extension for grasping by the user can be contemplated. A protrusion 305 having a prescribed shape can be fixed to or integral with the positioner 300. As shown in FIG. 3a, the protrusion 305 can be in the shape of a cone and can be fixed on one of the handles, namely handle 304. A cephalometric mount 110 can be affixed to a vertically adjustable base (not shown). Two rails 111 and 112 (on a lower surface of the mount 110) can allow the engagement and the sliding of respectively a collimator (not e.g., collimator 12) to shape the x-ray beam and an x-ray cephalometric sensor (e.g., sensor 13) having the shape of a thin rectangle. A cephalometric x-ray image is obtained by performing a scanning process including the accumulation of frames of the patient's skull or hand obtained continuously while the cephalometric sensor and the cephalometric collimator slide in a synchronized movement. In FIGS. 3a-3b, a housing 114 of the mount 110 can be dedicated to attach or fix a patient's head positioning unit (not shown) (e.g., system 14) and a housing 113 can be provided for engaging the protrusion 305 of the hand positioner 300. FIG. 3b represents the ensemble composed of the cephalometric mount 110 and the hand's positioner 300 in the engaged position with the protrusion 305 in the housing 113 (e.g., with prescribed matching or interlocked shapes).

Figure 4:
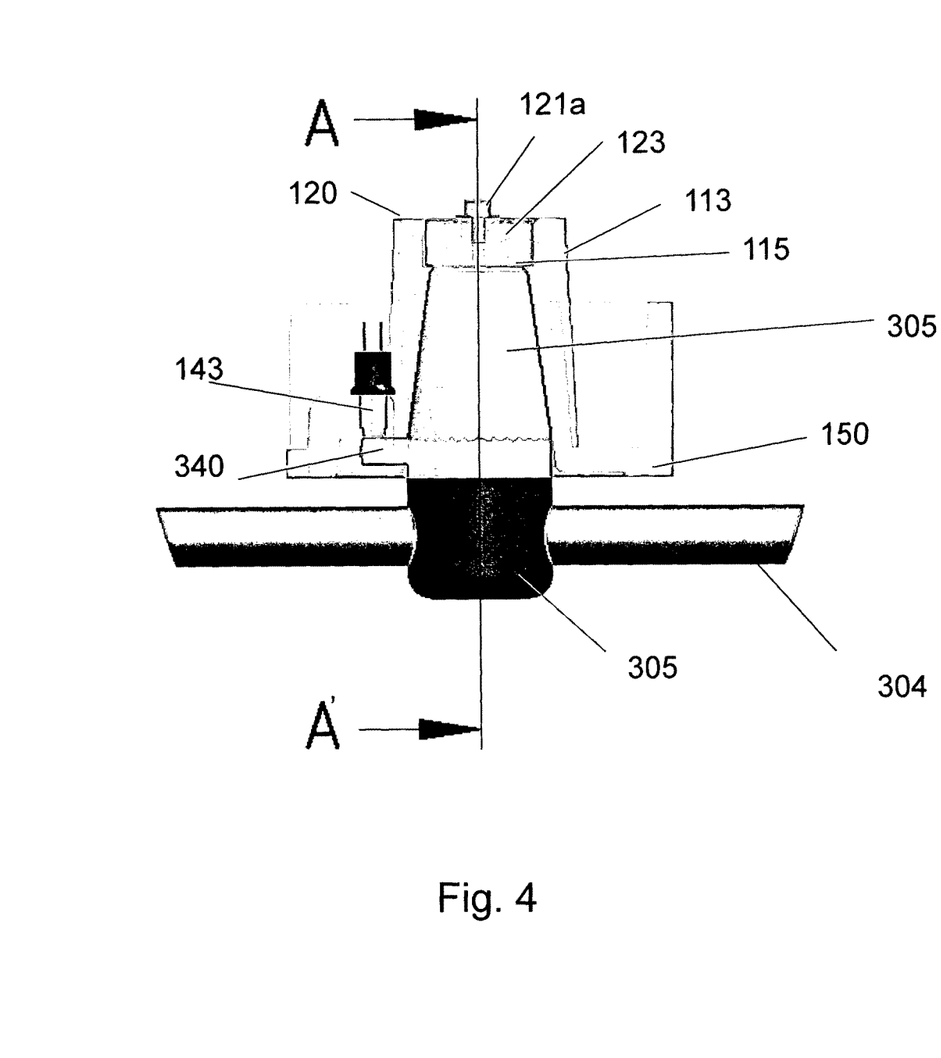
FIG. 4 is a diagram that shows an enlarged view of the engagement of an exemplary hand positioner embodiment on the cephalometric mount.
Figure 5:
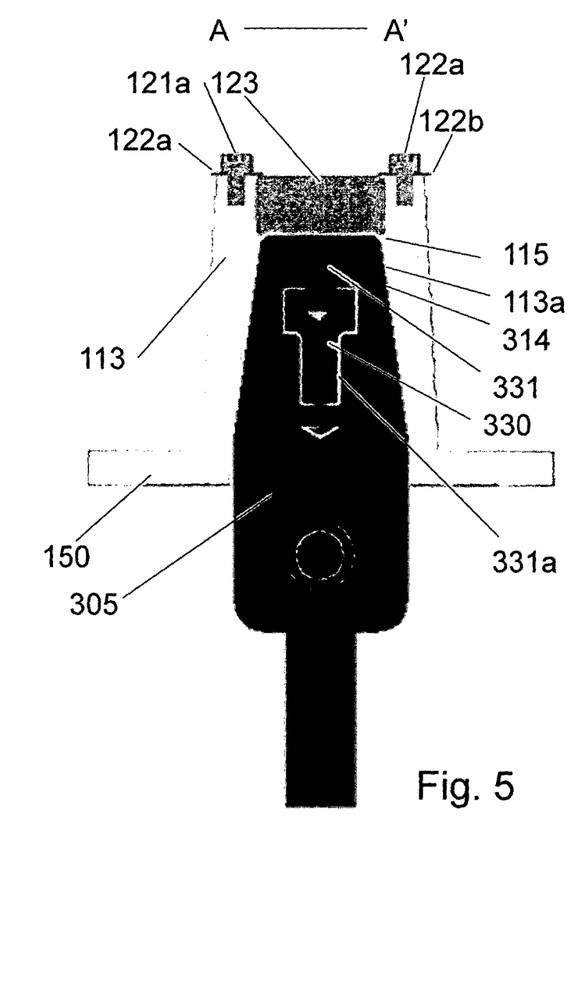
FIG. 5: is a diagram that shows a cross section of engagement of the hand's positioner on the cephalometric mount.

FIG. 4 shows an enlarged view of the engagement of an exemplary hand positioner embodiment on the cephalometric mount. FIG. 5 shows a cross section of engagement of the hand positioner of FIG. 4 along line A-A'.

As shown in FIGS. 4-5, a surface 150 of the cephalometric mount 110 can be provided with the housing 113 having an interior surface or bore in the shape of a hollow recess. The inner shape of the hollow recess in the housing 113 can have the general shape of a tapering conical bore 113a. In one embodiment, a permanent magnet 123 is positioned or fixed within the hollow recess or tapering conical bore 113a. As shown in FIG. 4, the permanent magnet 123 can be mounted (e.g., bottom surface) between a shoulder 115 provided inside the tapering conical bore 113a and (top or opposite surface) at least one fastener. As shown in FIGS. 4-5, the top surface of the magnet 123 is held against two screws 121a and 121b. For example, the two screws 121a and 121b are fixed at diametrically opposed positions of the top surface 120 and press two rings 122a and 122b against the permanent magnet 123 (e.g., top surface). Again, the magnet 123 can be sandwiched between the shoulder 115 and the two rings 122a and 122b. In one embodiment, the top surface of the permanent magnet 123 slightly raises over (e.g., exceeds) the circular top surface 120 of the tapering conical bore 113a. In one embodiment, the shoulder 115 extends only slightly into the tapering conical bore 113a so that a majority or substantially all of the permanent magnet 123 is exposed in the bore 113a. Alternatively, the shoulder 115 can cover, for example, 20%, most or all of the permanent magnet 123. In addition, other known methods of mounting the magnet 123 in the housing 113 can be used.

In the installed or engagement position of the hand positioner 300 in the cephalometric mount 110, the protrusion 305 of the hand positioner 300 can penetrate inside the conical bore 113a of the housing 113. In one embodiment, the protrusion 305 can be made of aluminum and fixed on the handle 304 of the hand positioner 300. In certain exemplary embodiments, an outer lateral face 314 of the protrusion 305 can mate or engage with the inner face of the bore 113a, and preferably, the top face of the protrusion 305 comes into contact (or magnetic engagement) with the lower face of the permanent magnet 123. The protrusion 305 is provided with a mounting end 331 extending along an axis of symmetry of the protrusion 305. The mounting end 331 can include a threaded part 331a. A magnetic part can be inside the mounting end 331. As shown in FIG. 5, a magnetic screw 330 (e.g., iron screw) can be screwed inside the threaded bore 331. When the protrusion 305 is mounted in the mount 10, a magnetic attraction is exerted by the permanent magnet 123 on the magnetic screw 330.

Advantageously, the position of the magnetic screw 330 inside the threaded bore 331 of the protrusion 305 can be modified to change and/or monitor the magnetic attraction by the permanent magnet 123. On the one hand, the magnetic screw 330 must be close enough to the magnet 123 so that the attraction counter-balances the weight of the whole hand positioner 300. As held by the magnet 123 in the mounted position at the mount 110, the hand positioner 300 is ready to be used for an x-ray imaging of the hand and the carpus of the patient. On the other hand, when the magnetic screw 330 is positioned too close to the magnet 123, the attraction force can be too heavy and the dentist will have some difficulties to remove the hand positioner 300 from the cephalometric mount 110 (e.g., at the end of the carpus imaging process). Further, adjustment of the attraction force can be manually (or automatically) performed by manually moving (e.g., turning, sliding) the magnetic screw to be closer or further from the magnet 123 when mounted. In one embodiment, the adjustable attracted engagement force can be adjusted by increasing or decreasing a 3D distance between the attracted member and the magnetic attractor. Alternative ways of adjusting the attraction force can be contemplated, for example, by adding additional or removing magnetically attractable material to the protrusion 305 or the like. Advantageously, exemplary system and/or method embodiments according to the application can allow an easy positioning and/or easy removal of the hand positioner 300 compared to the complicated and bulky mechanisms of the prior art.

It is of primary importance that the x-ray transparent plate 302 is parallel to the x-ray cephalometric sensor (not represented, sensor 13) engaged in the rail 112 so that the hand is projected on the plane of the cephalometric sensor without overlap of anatomical structures of the hand or the carpus. For this purpose, certain exemplary apparatus and/or method embodiments of the application provide a single mounting orientation and/or an sensory indication of proper mounting or installation of the hand positioner 300.

Figure 6:
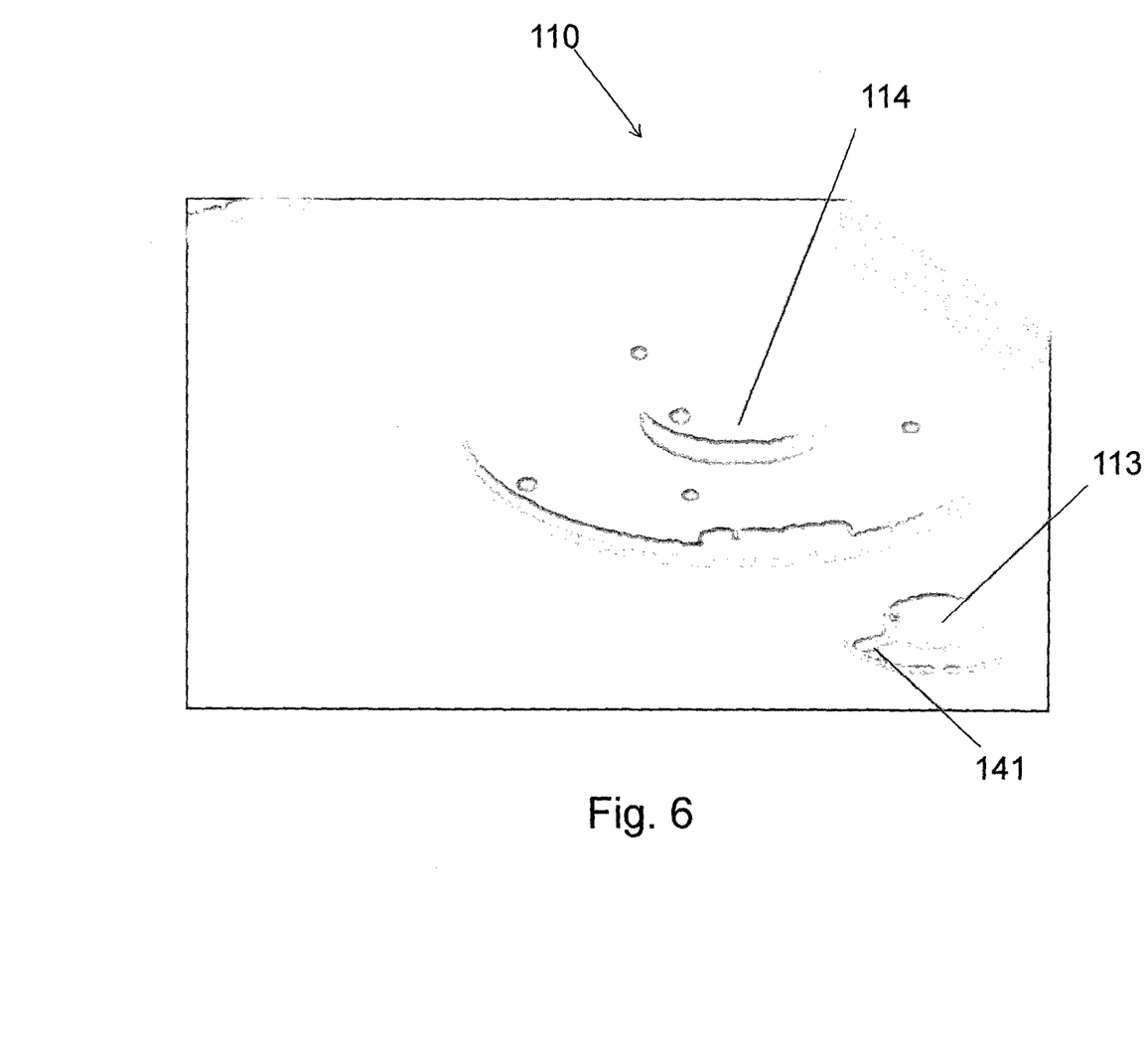
FIG. 6 is a diagram that shows an enlarged view of the cephalometric mount representing the slit to engage an arm of an exemplary hand positioner embodiment in correct angular orientation.

FIG. 6 is a diagram that shows an enlarged view of the cephalometric mount representing a recess (e.g., slit) to engage an extension (e.g., arm) of an exemplary hand positioner embodiment in correct angular orientation. In one embodiment, a transverse bar 340 extends orthogonally away from the protrusion 305 (see FIG. 4). As shown in FIG. 6, the transverse bar 340 is configured to engage the slot 141 made on the surface 150 of the cephalometric mount 110 that joins (e.g., extends from) the bore 113a of the housing 113. Preferably, the hand positioner 300 can be engaged in the bore 113a of the housing 113 on the surface 150 of the cephalometric mount 110 in one single possible angular position, ensuring that the surface 302 of the hand positioner 300 is parallel to an imaging plane of the cephalometric sensor.

Figure 7:
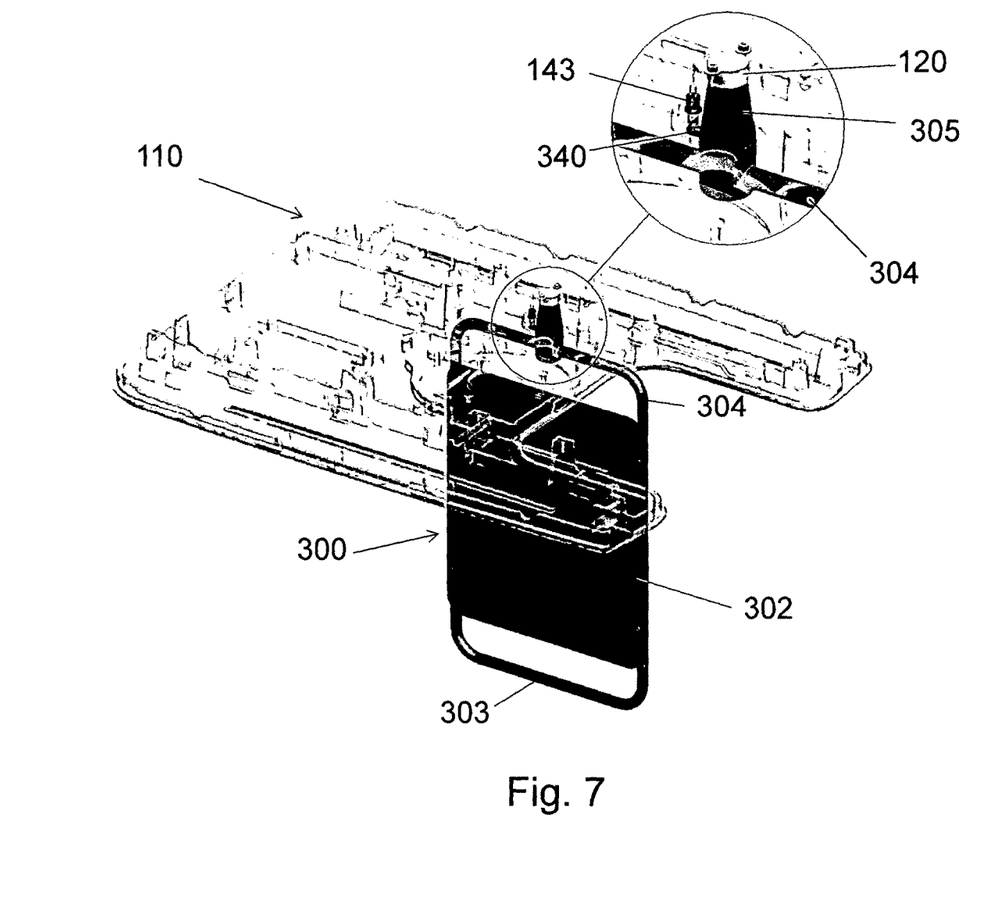
FIG. 7 is a diagram that shows an exemplary hand positioner embodiment engaged in the cephalometric mount, the cephalometric mount being represented in transparency.

Further, the dentist needs to be informed that the hand positioner 300 is conveniently positioned or properly mounted in the cephalometric mount 110. For this purpose, in certain exemplary system and/or method embodiments, an indicator to verify mounting of the positioner 300 can be built into the cephalometric mount 110 or the hand positioner 300. In one embodiment, an electrical switch 143 is provided on the surface 150 of the mount 110 at the vicinity of the housing 113. The electrical switch 143 can include a contact that extends up to the slot 141 (see FIGS. 4 and 7).

When the hand positioner 300 is engaged to the mount 110, the transverse bar 340, which is electrically conductive, comes into contact with the contact of electrical switch 143, and consequently an electrical current travels through the switch 143 to be indicative of the correct engagement of the hand positioner 300. A corresponding information for the dentist can be displayed on a user's interface like a computer screen or using a visual indicator (e.g., light, red/green, etc.). Alternatively, an audible alert or corresponding information for the dentist can be broadcast on a user's interface like a speaker. In one embodiment, the transverse bar 340 can be metallic or a conductive layer over at least one insulating or non-conductive core.

Consistent with exemplary embodiments of the application, a computer program utilizes stored instructions that perform on image data that is accessed from an electronic memory. As can be appreciated by those skilled in the image processing arts, a computer program for operating the imaging system in an exemplary embodiment of the present application can be utilized by a suitable, general-purpose computer system, such as a personal computer or workstation. However, many other types of computer systems can be used to execute the computer program of the present application, including an arrangement of networked processors, for example. The computer program for performing exemplary methods/apparatus of the present application may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing exemplary methods/apparatus of the present application may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present application may make use of various image manipulation algorithms and processes that are well known.

It will be further understood that the computer program product embodiment of the present application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present application, are not specifically shown or described herein and may be selected from such algorithms, systems, hardware, components and elements known in the art.

In certain exemplary embodiments, the first patient positioning and holding system 6 can include a substantially transparent shield suspended from the mount 2 or the rotatable gantry 3, and a chin positioning element that can include a chin rest and a bite element. In one embodiment, the shield can include an open window disposed between a chin support and a forehead support. In one embodiment, the shield can be visibly transparent, transparent to additional radiation including x-rays and/or formed from a molded polycarbonate material. In one embodiment, the chin support can include a height adjuster for the bite element and the forehead support is configured to be adjustably pivotable toward the patient. In one embodiment, the shield can include one or more controls for setting a column height adjustment for the mount on the shield or mounted on a separate panel that is coupled to the shield. In one embodiment, the shield can include one or more markings to assist in patient positioning. In one embodiment, the shield can include a first Frankfort plane positioning indicator.

In certain exemplary embodiments, an extra-oral imaging system can include a support base adjustable in at least one dimension; a first mount mounted to the support base and configured to revolve an x-ray source and an imaging sensor panel about an imaging area; and a first patient positioning unit coupled to the extra-oral imaging system and positioned between the x-ray source and first sensor so that x-rays impinge the first sensor after radiating the imaging area, including a chin support coupled to the first patient positioning unit and includes a chin positioning element; a head support coupled to the first patient positioning unit shield; and a first Frankfort plan positioning indicator; a second mount mounted to the support base and configured to position a second imaging sensor panel about a second imaging area; and a second patient positioning unit coupled to the second mount and positioned between the x-ray source and the second sensor so that x-rays impinge the second sensor after radiating a second imaging area including a head support coupled to the second patient positioning unit; and a second Frankfort plane positioning indicator. In one embodiment, the second Frankfort plane positioning indicator is fixedly mounted, detachably mounted, or mounted to move between at least two positions, or rotatably mounted. In one embodiment, the second patient positioning unit is configured to repeatably and accurately position a patient between the x-ray source and the second imaging sensor panel.

The invention has been described in detail, and may have been described with particular reference to an exemplary or presently preferred embodiment, but it will be understood that variations and modifications can be effected within the spirit and scope of the invention. For example, exemplary hand positioner device embodiments disclosed herein use a single arm and movement in a single direction to mount to the cephalometric mount. Alternatively, exemplary hand positioner device embodiments could use two or dual movements in orthogonal directions to install into the cephalometric mount with a selected orientation (e.g., without tools) and for example, gravity and a notched position to hold the prescribed alignment. Further, in certain selected embodiments, the hand positioner device can include a mounting recess and an elongated recess oriented to extend along a first direction, where the cephalometric mount comprises an extension, and where the hand positioner device can be mounted to the cephalometric mount only when the extension is aligned with the first direction. In addition, exemplary apparatus and/or method embodiments according to the application have been described relative to a combined cephalometric, panoramic and computed tomography dental imaging apparatus, but are intended to be applicable to stand-alone cephalometric imaging apparatus or cephalometric imaging apparatus with any additional mode(s) of operation or functionality. The presently disclosed exemplary embodiments are therefore considered in all respects to be illustrative and not restrictive. Alternatives to using a magnetic force can also be contemplated. The scope of the invention is indicated by the appended claims, and all changes that come within the meaning and range of equivalents thereof are intended to be embraced therein.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

The invention claimed is:

1. An extra-oral imaging system, the extra-oral system comprising:
a support base adjustable in at least one dimension;
a cephalometric module coupled to the support base and configured to position a cephalometric imaging sensor about a first imaging area formed with an x-ray source, where x-rays from the x-ray source impinge the cephalometric sensor after radiating the first imaging area;
a cephalometric patient positioning unit positioned operatively near the first imaging area;
a cephalometric collimator; and
a hand positioner device detachably coupled to the cephalometric module between the collimator and the cephalometric sensor, where the hand positioner device is removed by applying force to the hand positioner device in a single direction.

2. The extra-oral imaging system of claim 1, where the hand positioner device is attached or removed without using tools.

3. The extra-oral imaging system of claim 2, where an engagement force between the hand positioner device and the cephalometric mount is adjustable within a range.

4. The extra-oral imaging system of claim 3, where an engagement force between the hand positioner device and the cephalometric mount is adjustable within the range without using tools.

5. The extra-oral imaging system of claim 1, where the hand positioner device is removed when the force is greater than a threshold force, where the threshold force is related to a magnetic force between the cephalometric module and the hand positioner device.

6. The extra-oral imaging system of claim 1, where an engagement force between the hand positioner device and the cephalometric mount comprises a magnetic attractor and an adjustable attracted member, where the magnetic attractor is attached to the cephalometric mount and the adjustable attracted member is mounted in the hand positioner device, where a distance from the attracted member to the magnetic attractor is controlled by adjusting a position of the attracted member in the hand positioner device.

7. The extra-oral imaging system of claim 6, where the adjustable attracted engagement force is adjusted by increasing or decreasing a 3D distance between the attracted member and the magnetic attractor.

8. The extra-oral imaging system of claim 1, where the hand positioner device can be mounted only in a single position parallel to the cephalometric sensor.

9. The extra-oral imaging system of claim 8, where the cephalometric mount comprises an elongated recess oriented to extend along a first direction, where the hand positioner device comprises an extension, and where the hand positioner device can be mounted to the cephalometric mount only when the extension is aligned with the first direction.

10. The extra-oral imaging system of claim 8, where the hand positioner device comprises an elongated recess oriented to extend along a first direction, where the cephalometric mount comprises an extension, and where the hand positioner device can be mounted to the cephalometric mount only when the extension is aligned with the first direction.

11. The extra-oral imaging system of claim 1, where the cephalometric module includes a recess with a prescribed asymmetric shape, and the hand positioner device includes an asymmetric extension that mounts to the recess in a single orientation of the hand positioner device.

12. The extra-oral imaging system of claim 1, where concurrent and detectable information is provided when the hand positioner is installed for subsequent imaging operations.

13. The extra-oral imaging system of claim 12, where the concurrent and detectable information is a visual indication or an audible indication when the hand positioner is installed to the mount.

14. The extra-oral imaging system of claim 1, where the cephalometric patient positioning unit is between the integral cephalometric collimator and the cephalometric imaging sensor, where the cephalometric patient positioning unit comprises:
 a forehead support, the forehead support is adjustable in at least two dimensions; and
 at least one temporal holding member adjustable in at least one dimension; and
 a retractable cephalometric Frankfort plane positioning indicator, where the retractable cephalometric Frankfort plane positioning indicator is configured to be mounted to one or both sides of the integral cephalometric collimator.

15. The extra-oral imaging system of claim 1, comprising:
 a first mount mounted to the support base and configured to revolve the x-ray source and an imaging sensor about a second imaging area so that x-rays impinge the imaging sensor after radiating the second imaging area; and
 a second patient positioning unit coupled to the extra-oral imaging system and positioned operatively near the second imaging area, comprising:
 an elongated shield comprising handles;
 a chin support coupled to the elongated shield and comprising a chin positioning element; and
 a head support coupled to the elongated shield; and
 a second Frankfort plan positioning indicator.

* * * * *